United States Patent [19]

Gray et al.

[11] 3,996,225

[45] Dec. 7, 1976

[54] MANUFACTURE OF CYANURIC ACID

[75] Inventors: Charles A. Gray, Princeton; Sidney Berkowitz, Highland Park; James Lawrence Manganaro, East Windsor, all of N.J.

[73] Assignee: FMC Corporation, Philadelphia, Pa.

[22] Filed: Dec. 9, 1975

[21] Appl. No.: 639,082

[52] U.S. Cl. ............................................ 260/248 A
[51] Int. Cl.$^2$ ...................................... C07D 251/32
[58] Field of Search ............................... 260/248 A

[56] References Cited
UNITED STATES PATENTS 3,835,136   9/1974   Hirdler et al. ..................... 260/248

*Primary Examiner*—John M. Ford

[57] ABSTRACT

Waste digester liquor, containing dissolved triazines, ammonium salts and iron, is treated with a mineral base until the pH is about 2.5 to 4 whereby triazines are precipitated while most of the iron remains dissolved. The triazines are separated and recycled back to the digester. The pH of the filtrate is increased to about 11 and the ammonia stripped off and recovered leaving an essentially nitrogen free aqueous solution. This can be sewered directly or concentrated to recover the salts.

4 Claims, No Drawings

MANUFACTURE OF CYANURIC ACID

This invention relates to the manufacture of cyanuric acid. More particularly, it is concerned with recovering useful and valuable products from such waste streams while ameliorating pollution.

Cyanuric acid is an important chemical commodity, the principal use of which is in the production of chlorinated cyanurates, a family of commercial dry bleaches. In fact, industry sources estimate that 90% of the total output is converted to chlorinated derivatives while the remainder finds application as a chlorine stabilizer for swimming pools and as a starting material for organic syntheses.

Although obtainable by a variety of reactions, cyanuric acid is made commercially by the pyrolysis of urea in accordance with the following scheme:

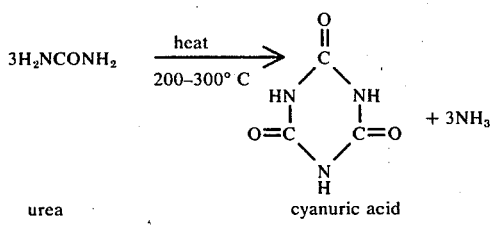

However, the reaction does not lead exclusively to cyanuric acid, but yields various by-products, notably the aminotriazines ammelide, ammeline and melamine. By employing the latest improvements in processing and reactor design, the urea pyrolysis can be optimized whereby a product is obtained assaying at about 80% cyanuric acid; about 17% ammelide; about 2% ammeline and less than about 1.0% melamine. This crude material is treated with an acidic solution such as digestion with dilute mineral acid whereby the aminotriazines are hydrolyzed to cyanuric acid. The resulting slurry is separated, washed free of acid and dried to give essentially pure cyanuric acid. For a fuller treatment on the chemistry and manufacture of cyanuric acid, reference is made to Kirk-Othmer Encyclopedia of Chemical Technology, Vol. 20, 2nd Revised Ed. 1969, pages 662-671 and to the bibliography appended thereto.

Although the manufacture of cyanuric acid by the pyrolysis of urea is generally a successful commercial process, there is still considerable need for improvement in handling the waste stream which remains after separating the cyanuric acid from the acid digestion. Such waste stream, commonly referred to as waste digester acid, is an acidic aqueous solution containing ammonium salts, triazines of the group cyanuric acid and aminotriazines and iron. A representative plant specimen produced from mineral acid digestion consists essentially of about 10 to 20% by weight of the mineral acid; about 4 to 8% by weight of an ammonium acid salt of said acid; about 1-4% by weight of the triazines ammelide, cyanuric acid, ammeline and melamine in decreasing order of concentration plus about 50-70 ppm of iron while the remainder is water. Considering that the nitrogen assay of waste digester acid discharged from a modern cyanuric acid plant is about one pound of total nitrogen (Kjeldahl) per 10-20 pounds of product, the loss in valuable nitrogen compounds, i.e. ammonium salts and triazines, is indeed substantial.

There have been proposals for recovering nitrogen values from triazine waste streams. For instance, in USSR Pat. No. 345,103 there is described a process of treating alkaline waste streams containing melamine, ammeline, ammelide and cyanuric acid by contacting the streams with carbon dioxide to adjust the pH to about 8 whereby most of the triazines are precipitated; melamine is isolated as its cyanuric salt. After separation of precipitated triazines, the filtrate is heated at 120°–200° C in aqueous alkali to hydrolyze the remaining dissolved triazines to ammonia, carbon dioxide and water. Final traces of triazines are removed by adsorption on activated carbon after which the waste waters are essentially free of organics and can be discharged into the environment.

The technique aforesaid of recovering triazine values from alkaline waste streams is not applicable to waste digester acid from cyanuric acid manufacture. In the first place, the alkali needed to bring the pH of the waste digester acid up to 8 would increase plant overhead substantially. Moreover, the recovered triazines would be contaminated with iron compounds which are insoluble in an alkali medium.

In accordance with the present invention, it has been discovered that in the manufacture of cyanuric acid wherein urea is pyrolyzed to produce crude cyanuric acid which is then treated with an acidic aqueous solution to give purified cyanuric acid and waste digester acid containing dissolved ammonium salts, triazines of the group cyanuric acid and aminotriazines and iron, such waste digester acid can be converted into useful products and an aqueous effluent having essentially zero nitrogen loading comprising the steps: (a) adjusting the pH of the waste stream to a range of about 2.5 to about 4.0 by contacting it with a mineral base, capable of forming soluble salts with the acid in the waste digester acid, whereby there is precipitated a substantial amount of the triazines and a minor amount of the iron; (b) separating the precipitated triazines and iron from the aqueous filtrate containing the remainder of iron and triazines; (c) adding mineral base to the filtrate until sufficiently alkaline to convert nitrogen values to ammonia; (d) stripping and recovering the ammonia thereby leaving an essentially aqueous solution of a salt derived from the mineral base.

In carrying out the process of the invention, the waste digester acid is mixed with the mineral base until the pH of the mixture is in the range of about 2.5 to 4.0. By operating at these pH levels, it is possible to effect precipitation of a substantial amount of the triazines and a minor amount of iron. As understood herein, a substantial amount when applied to a waste digester acid component means about 50% by weight while a minor amount means less than 50% by weight.

The mineral base can be any alkaline material which forms soluble salts with the acid component in the waste digester acid. Normally, the mineral base is a hydroxide or weak acid salt of the alkali or alkaline earth metals; a preferred member is sodium hydroxide.

The co-precipitation of iron can be prevented or at least greatly suppressed by introducing the mineral base to the waste liquor in the presence of a chelating agent, such as citric acid, capable of forming a soluble iron complex. However, this feature adds to the cost of the process and the presence of a chelating agent may reduce the nitrogen assay of some of the recovered products.

Following the treatment with mineral base, the precipitated triazines are isolated from the reaction mixture by the usual procedures for separating solids from a liquid substrate such as filtration, centrifugation, decantation, or the like.

The process of the invention is applicable to batch and continuous operations. Generally, its greatest utility is realized when incorporated as an adjunct in the continuous large scale manufacture of cyanuric acid in which precipitated triazines are recycled back to the acid digester for conversion into cyanuric acid.

As previously pointed out, the waste digester acid discharged from the digestion of cyanuric acid is an acidic aqueous solution containing dissolved triazines of the group cyanuric acid and aminotriazines, iron and ammonium salts formed by the acid hydrolysis of the aminotriazines in the crude cyanuric acid. Generally, the acid used in current commercial practice is sulfuric acid although other mineral acids, notably, phosphoric acid are satisfactory also.

The filtrate remaining after separating the precipitated solids in accordance with the process herein is an aqueous solution of unprecipitated iron and triazines, primarily cyanuric acid with only trace amounts of ammelide and ammeline and perhaps a trace of melamine plus ammonium salts and salts derived from the mineral base. The composition of the ammonium salts, that is, whether acid or neutral salts will vary with the pH of the waste stream after addition of the mineral base. Thus, where sulfuric was used in the digestion, the ammonium salts in the aforetreated waste stream will be a mixture of ammonium sulfate and ammonium bisulfate.

The filtrate is next made highly alkaline, at least pH 11, with mineral base such as sodium hydroxide and the released ammonia stripped off and recovered in the usual manner. Where stripping is effected below about 200° C, the evolved ammonia comes solely from the ammonium salts. If, on the other hand, the temperature exceeds about 200° C, residual triazines will be hydrolytically cleaved thereby providing an additional small increment of ammonia.

After the ammonia has been stripped, there remains an aqueous solution of the mineral base and salts formed from the neutralization of the waste digester acid. This alkaline aqueous solution can be discharged into the environment since it is essentially free of nitrogen compounds and organic matter. In some instances, depending on the local economic situation, it may be feasible and even profitable to concentrate the effluent and recover the solid salt, particularly if it is sodium sulfate which has market value.

The process of the present invention thus provides an answer as to what to do with the enormous volume of non-disposable waste digester acid from the manufacture of cyanuric acid by converting it into useful and valuable products and an environmentally compatable effluent.

The following non-limiting examples illustrate the invention in greater detail. All parts are by weight unless otherwise stated.

EXAMPLES 1 – 11

A specimen of waste digester acid, taken from the digester stage of a commercial cyanuric plant, was analyzed and found to have the following specifications:

| | |
|---|---|
| $H_2SO_4$ | 14.4% |
| $NH_4HSO_4$ | 5.0% |
| $(NH_4)_2SO_4$ | 0.07% |
| Cyanuric Acid | 0.27% |
| Ammelide | 0.04% |
| Ammeline | 0.090% |
| Melamine | 0.001% |
| Water | & remainder |
| pH | & 0.5 |

Each of several samples of the digester acid aforesaid was treated with 50% sodium hydroxide solution and the pH adjusted to increasing levels up to 8.5. After reaching the desired pH for a given sample, the reaction mixture was allowed to equilibrate for at least 24 hours at 23° C with any solid phase that had formed. At the end of this period, each of the reaction mixtures was filtered to remove solids and the filtrate analyzed by UV spectrophotometer. The analytical results are summarized in Table I.

EXAMPLES 12 – 25

The procedure of Examples 1–11 was repeated but in this case the purpose was to determine the iron remaining in solution after adding sodium hydroxide to samples of waste digester acid. Sufficient base was used to raise the pH of each successive sample by 0.5 pH units commencing with a pH of 0.5 for the untreated acid and a final pH of 8.5. The iron analyses (atomic absorption method) at the various pH levels are listed in Table II.

As is evident from the analytical date of Table II, almost all of the iron remains in solution over the pH range of about 2.5 to 4.0. However, once the upper pH limit of this range is exceeded, iron precipitation begins to build up rapidly thereby contaminating the recovered triazines and rendering them unsuitable for recycling back to the cyanuric acid digester.

The data in Table I demonstrate that a significant quantity of triazines are precipitated in the pH range of about 2.5 to 4. For instance, neutralization of waste digester acid to a pH of 4.0, reduces the amount of dissolved from 0.401 triazines to 0.213% which means that 0.198% or about 50% is precipitated and recovered for recycle back to the digester. Under these same pH conditions, however, only a very small quantity of iron is precipitated as is readily evident from the iron analysis of Table II. Note Example 16 which shows that at pH 4.0, 72.3% iron remains in solution.

The present invention thus provides the pH conditions whereby triazines, suitable for recycle, can be precipitated from iron contaminated waste digester acid coupled with ammonia recovery from dissolved nitrogen species. In addition to there valuable by-products, a final effluent is produced consisting essentially of an aqueous salt solution which has greater environmental compatability than the original waste stream.

TABLE I

COMPOSITION (%) OF WASTE DIGESTER ACID AFTER NEUTRALIZATION WITH SODIUM HYDROXIDE

| Example | pH | Ammelide | Cyanuric Acid | Ammeline | Melamine | Total Triazine |
|---|---|---|---|---|---|---|
| Untreated Digester Acid | 0.5 | 0.04 | 0.27 | 0.09 | 0.001 | 0.401 |
| 1 | 3.5 | 0.02 | 0.20 | 0.009 | 0.001 | 0.230 |
| 2 | 4.0 | 0.002 | 0.20 | 0.011 | 0.0 | 0.213 |
| 3 | 4.5 | 0.0 | 0.22 | 0.009 | 0.0 | 0.229 |
| 4 | 5.0 | 0.0 | 0.22 | 0.003 | 0.005 | 0.228 |
| 5 | 5.5 | 0.0 | 0.22 | 0.003 | 0.005 | 0.228 |
| 6 | 6.0 | 0.0014 | 0.16 | 0.002 | 0.001 | 0.164 |
| 7 | 6.5 | 0.0015 | 0.16 | 0.001 | 0.001 | 0.164 |
| 8 | 7.0 | 0.002 | 0.17 | 0.003 | 0.001 | 0.176 |
| 9 | 7.5 | 0.003 | 0.14 | 0.002 | 0.001 | 0.145 |
| 10 | 8.0 | 0.003 | 0.14 | 0.004 | 0.001 | 0.148 |
| 11 | 8.5 | 0.009 | 0.14 | 0.003 | 0.001 | 0.153 |

TABLE II

IRON CONCENTRATION OF WASTE DIGESTER ACID AFTER NEUTRALIZATION WITH SODIUM HYDROXIDE (at 23° C)

| Example | pH | % Fe Remaining in Solution |
|---|---|---|
| Untreated Digester Acid | 0.5 | 100 |
| 12 | 2.0 | 96.8 |
| 13 | 2.5 | 95.9 |
| 14 | 3.0 | 90.3 |
| 15 | 3.5 | 74.5 |
| 16 | 4.0 | 72.3 |
| 17 | 4.5 | 67.3 |
| 18 | 5.0 | 15.6 |
| 19 | 5.5 | 5.05 |
| 20 | 6.0 | 2.0 |
| 21 | 6.5 | 0.7 |
| 22 | 7.0 | 0.6 |
| 23 | 7.5 | 0.56 |
| 24 | 8.0 | 0.16 |
| 25 | 8.5 | 0.15 |

What is claimed is:

1. In the manufacture of cyanuric acid wherein urea is pyrolyzed to produce crude cyanuric acid and the crude cyanuric acid treated with an aqueous acidic solution to give purified cyanuric acid and a waste digester acid stream containing dissolved ammonium salts, triazines of the group cyanuric acid, and aminotriazines and iron, the improvement of converting the waste stream into useful products and an effluent of diminished nitrogen loading comprising the steps:

a. adjusting the pH of the waste digester acid to a range of about 2.5 to about 4.0 by contacting it with a mineral base whereby there is precipitated a substantial amount of the triazines and a minor amount of the iron;

b. separating the precipitated triazines and iron from the aqueous solution containing ammonium salts, and the remainder of iron and the triazines; and c. increasing the pH of the aqueous solution of iron and triazines from step (b) to at least about 11 and stripping off ammonia thereby leaving an aqueous salt solution derived from the mineral base having diminished nitrogen content.

2. The method of claim 1 wherein the mineral acid is sulfuric.

3. The method of claim 1 wherein the mineral base is sodium hydroxide.

4. The method of claim 1 wherein the aqueous solution is evaporated to recover the salts.

* * * * *

UNITED STATES PATENT OFFICE
CERTIFICATE OF CORRECTION

PATENT NO. : 3,996,225
DATED : December 7, 1975
INVENTOR(S) : C.A. Gray, S. Berkowitz, J. L. Manganaro It is certified that error appears in the above-identified patent and that said Letters Patent are hereby corrected as shown below:

Column 3, line 64, "compatable" should read --compatible--; column 4, lines 15 & 16, "Water     & remainder"
                                                                    "pH        & 0.5"          should read
--Water       remainder--
--pH          0.5--;   column 4, line 41, "date" should read
--data--; column 4, line 65, "there" should read --these--;
column 4, line 68, "compatability" should read
--compatibility--.

Signed and Sealed this

Third Day of May 1977

[SEAL]

Attest:

RUTH C. MASON
Attesting Officer

C. MARSHALL DANN
Commissioner of Patents and Trademarks